(12) United States Patent
Stothard et al.

(10) Patent No.: US 7,995,204 B2
(45) Date of Patent: Aug. 9, 2011

(54) DETECTOR/IMAGER

(75) Inventors: David Stothard, Fife (GB); Malcolm Dunn, Fife (GB); Cameron Rae, Fife (GB)

(73) Assignee: The University Court of the University of St. Andrews, St. Andrews (GB)

( * ) Notice: Subject to any disclaimer, the term of this patent is extended or adjusted under 35 U.S.C. 154(b) by 796 days.

(21) Appl. No.: 11/814,655

(22) PCT Filed: Nov. 29, 2005

(86) PCT No.: PCT/GB2005/004553
§ 371 (c)(1),
(2), (4) Date: Apr. 4, 2008

(87) PCT Pub. No.: WO2006/061567
PCT Pub. Date: Jun. 15, 2006

(65) Prior Publication Data
US 2009/0141281 A1    Jun. 4, 2009

(30) Foreign Application Priority Data
Dec. 6, 2004    (GB) .................................. 0426662.3

(51) Int. Cl.
*G01N 21/00*    (2006.01)

(52) U.S. Cl. ........................ 356/342; 356/433; 356/437
(58) Field of Classification Search .................. None
See application file for complete search history.

(56) References Cited

U.S. PATENT DOCUMENTS

| | | | | |
|---|---|---|---|---|
| 5,696,778 | A * | 12/1997 | MacPherson | 372/4 |
| 6,360,949 | B1 * | 3/2002 | Shepard et al. | 235/462.43 |
| 6,935,566 | B1 * | 8/2005 | Mulla et al. | 235/472.01 |
| 2002/0080841 | A1 * | 6/2002 | Yin et al. | 372/75 |
| 2004/0252300 | A1 * | 12/2004 | Slater | 356/318 |
| 2004/0263959 | A1 * | 12/2004 | Dixon et al. | 359/385 |

OTHER PUBLICATIONS

Stothard et al., Comparison of continuous-wave optical parametric oscillators based on periodically poled LiNbO3 and periodically poled RbTiOAsO4 pumped internal to a high-power Nd-YVO4 laser, Oct. 2003, J. Optical Society of America, vol. 20, No. 10, pp. 2102-2108.*

Unknown author, Optical Parametric Oscillator pumped with a passively Q-switched microchip laser, May 5, 1998, Cleo '98/Tuesday Afternoon, p. 136.*

International Search Report for corresponding PCT/GB2005/004553 completed Mar. 6, 2006 by L. Plouzennec of the EPO.

Stothard, et al.: "*Hyperspectral Imaging of Gases with a Continuous-Wave Pump-Enhanced Optical Parametric Oscillator*"; Optics Express, vol. 12, No. 5, Mar. 8, 2004, pp. 947-955, XP002367551.

(Continued)

*Primary Examiner* — Gregory J Toatley
*Assistant Examiner* — Juan D Valentin

(57) ABSTRACT

A back scatter absorption detector/imager having an optical parametric device for generating sensing radiation, the optical parametric device having a nonlinear medium (NLC) and a pump wave laser source, the nonlinear medium (NLC) being able to generate a signal and an idler wave in response to being stimulated with the pump wave, thereby to generate sensing radiation, and a detector (D) for detecting any sensing radiation back-scattered from a target area, characterized in that the pump wave laser source and the nonlinear medium (NLC) are provided in the same optical cavity.

17 Claims, 1 Drawing Sheet

OTHER PUBLICATIONS

Stothard, et al.: *"Comparison of Continuous-Wave Optical Parametric Oscillators Based on Periodically Poled LiNb0 and Periodically Poled RbTi0As04 Pumped Internal to a High-Power Nd:YV04 Laser"*; Journal of the Optical Society of America B (Optical Physics), vol. 20, No. 10, Oct. 2003, pp. 2102-2108, XP002367552.

Anonymous: *"High Repitition Rate OPO"*; Internet Article, [Online], XP002367553, Retrieved from the Internet: URL: http://www.photonix.com/PDFs%20of%20Brochures/opo-ylf.pdf>, [Retrieved on May 17, 2004], Retrieved from the Internet: URL: http://www.photonix.com/PDFs%20of%20Brochures/opo-ylf.pdf>, [retrieved on Feb. 14, 2006].

Ebrahimzadeh, et al.: *"Intracavity Continuous-Wave Singly Resonant Optical Parametric Oscillators"*; Journal of the Optical Society of America B (Optical Physics), vol. 16, No. 9, Sep. 1999, pp. 1499-1511, XP002367554.

Bai, et al.: *"Compact Intracavity Pumped Continuous-Wave Singly Resonant PPLN OPO"*; May 17, 2004, Lasers and Electro-Optics, 2004. (CLEO). Conference on San Francisco, CA, USA May 20-21, 2004, Piscataway, NJ, USA, IEEE, pp. 109-110, CP010744995, ISBN: 1-55752-777-6; *Fig. 1*.

Peng, et al.: *"Compact Broadband Tunable Short Pulse High-Repetition-Rate Optical Parametric Oscillator"*; Environmental Monitoring and Remediation III Conference—Proceedings of SPIE, vol. 5270, Oct. 28, 2003, pp. 214-220, XP002367555; *Fig. 1*.

Marshall, et al.: *"Highly Efficient Optical Parametric Oscillators"*; Eyesafe Lasers: Components, Systems, and Applications Conference—Proceedings of SPIE, vol. 1419, 1991, pp. 141-152, XP002367556; *Fig. 4*.

Turnbull, et al.: *"Transient Dynamics of CW Intracavity Singly Resonant Optical Parametric Oscillators"*; IEEE Journal of Quantum Electronics, vol. 35, No. 11, Nov. 1999, pp. 1666-1672.

Kulp, et al.: *"Active Infrared Images Visualize Gas Leaks"*; Retrieved from the Internet Jun. 1996, pp. 1-4.

McRae, et al.: *"Backscatter Absorption Gas Imaging: A New Technique for Gas Visualization"*; Applied Optics, vol. 32, No. 21, Jul. 20, 1993, pp. 4037-4050.

Kulp, et al.: *"Active Infrared Imagers Visualize Gas Leaks"*; Laser Focus World, Jun. 1996, pp. 211-218.

Kulp, et al.: *"Development of a Pulsed Backscatter-Absorption Gas-Imaging System and Its Application to the Visualization of Natural Gas Leaks"*; Applied Optics, vol. 37, No. 18, Jun. 20, 1998, pp. 3912-3922.

Kulp, et al.: *"Portable Laser-Based Imager Offers Efficient Hydrocarbon Detection"*; Laser Focus World, www.laserfocusworld.com, Mar. 2004, pp. 93-98.

Kulp, et al.: *"Portable Laser-Based Imager Offers Efficient Hydrocarbon Detection"*; Mar. 2004, pp. 1-4.

Powers, et al.: *"Demonstration of Differential Backscatter Absorption Gas Imaging"*; Applied Optics, vol. 39, No. 9, Mar. 20, 2009, pp. 1440-1448.

Oshman, et al.: *"Theory of Optical Parametric Oscillation Internal to the Laser Cavity"*; IEEE Journal of Quantum Electronics, vol. QE-4, No. 8, Aug. 1968, pp. 491-502.

* cited by examiner

DETECTOR/IMAGER

The present invention relates to a back-scatter absorption detector/imager, and in particular a portable back-scatter absorption gas detector/imager.

BACKGROUND TO THE INVENTION

Back-scatter absorption gas imaging (BAGI) is a powerful technique for imaging gaseous species that are transparent in the visible wavelength band. Back-scatter absorption gas imagers generally include a source of spectrally pure light that is tuned into an absorption feature of the gas to be detected, and a detector for detecting light scattered from a target area. The detector may be a camera or some other imaging device for displaying an image of the target area. In use, the target area is illuminated with the spectrally pure light and the detector is positioned to detect any light which is back-scattered. If no gas is present, the light is back-scattered from the target and collected by the detector. In this case, a clear image of the target scene is displayed. In contrast, if gas is present then it will absorb the light and a dark area corresponding to the gas will appear on the image. In this way there is provided a simple and effective visual means for detecting gas.

The application of BAGI to hydrocarbon and in particular methane detection depends on the availability of an optical source that produces light in the mid-infrared band particularly over the wavelength range of 2-6 microns, where these gases exhibit strong absorption lines. The absorption linewidth associated with discrete absorption features in a gas such as methane is typically of the order of ~1 GHz due to Doppler broadening at low pressures. As the pressure is increased to normal air pressure, the linewidth increases to ~5 GHz due to pressure broadening. To detect such a single line absorption feature effectively it is therefore necessary to use an optical source that exhibits a spectral linewidth comparable to or less than this latter figure. Currently, there are no lasers that operate in the required wavelength range and have a suitable linewidth and tunability capability, whilst emitting sufficient power for practical use in back-scatter absorption gas imaging. Optical parametric oscillators (OPOs) are therefore employed in order to convert the wavelength from a parent pump laser operating at a wavelength that is shorter than required, into the spectral band of interest, that is to say frequency down-conversion. Optical parametric oscillators include a nonlinear medium that is operable to generate a signal and an idler wave in response to being stimulated with a laser pump wave source. In conventional OPOs, the pump wave source resides in a separate optical cavity to that of the nonlinear medium. These will be referred to as extra-cavity OPOs.

The current state of the art in the application of OPO's to BAGI has been developed by an American research group based at Sandia National Laboratories (SNL). This group has published numerous papers in this field, such as "Backscatter Absorption Gas Imaging—a New Technique for Gas Visualization" by T. G. McRae, and T. J. Kulp, Applied Optics, 1993. 32(21): p. 4037-4050; "Development of a pulsed back-scatter-absorption gas-imaging system and its application to the visualization of natural gas leaks" by T. J. Kulp et al., Applied Optics, 1998. 37(18): p. 3912-3922; "Active infrared imagers visualize gas leaks" by T. J. Kulp and T. McRae, Laser Focus World, 1996. 32(6): p. 211; "Portable laser-based imager offers efficient hydrocarbon detection" by T. J. Kulp et al, Laser Focus World, 1004. 40(3): p. 93-; and "Demonstration of differential backscatter absorption gas imaging" by Powers, P. E. et al, Applied Optics, 2000. 39(9): p. 1440-1448. In general, the SNL group has employed both continuous-wave and pulsed OPO's for the illumination source and focal-plane array cameras and rastering scanners for the imaging system. Although impressive results have been reported in terms of both the lower detectability limit and target range, the technology developed at Sandia National Laboratories is characterised by very high component costs, high system complexity, prohibitive power requirements and bulky designs. Such issues cast serious doubt over the possibility of developing such systems into truly portable ambulatory devices appropriate for field use.

Another OPO based BAGI technique is described in "Hyperspectral imaging of gases with a continuous-wave pump-enhanced optical parametric oscillator" by D. J. M. Stothard, M. H. Dunn, and C. F. Rae, Optics Express, 2004. 12(5): p. 947-955. This arrangement uses a pump enhanced continuous wave OPO. Whilst this arrangement provides an effective means for detecting gas, the optical requirements are such that the device is difficult to make fully portable. Clearly, this is a significant disadvantage.

An object of the present invention is to provide an improved back-scatter absorption detector/imager.

SUMMARY OF THE INVENTION

According to the present invention, there is provided a back scatter absorption detector comprising:
  an optical parametric device for generating sensing radiation, the optical parametric device having a nonlinear medium that is operable to generate a signal and an idler wave in response to being stimulated with a pump wave, wherein the pump wave laser source and the nonlinear medium are provided in the same optical cavity, and
  a detector for detecting any sensing radiation back-scattered from a target area.

Preferably, the detector includes means for displaying the output from the detector in the form of an image of the scene under surveillance in which, for example, a gas is rendered visible.

The detector/imager of the present invention has an optical parametric device for generating the sensing radiation with a laser gain medium and a nonlinear frequency conversion crystal in the same optical cavity. This is referred to as an intracavity OPO. Although it has not previously been reported in the art, the inventors have recognised that intracavity OPOs deliver adequately narrow linewidths with adequate frequency stability for imaging, including hydrocarbon gas imaging. By using an intra-cavity OPO, it is possible to take advantage of the high circulating field available within the laser cavity to bring the OPO to above threshold for efficient down-conversion without the requirement for high pump powers as is the case in extra-cavity devices. This means that a relatively low pump power can be used. This is desirable as it obviates penalties such as the need for water-cooling and, when running on batteries, reduced operation time. Further, the need for bulky, high power pump lasers is avoided. Similar considerations apply to the operation of continuous-wave OPO's. These features are particularly useful in the context of the present invention, as they mean that the imager can be made small, compact and readily portable, whilst at the same time being efficient and capable of producing significant optical powers.

Another advantage of the intracavity OPO not previously reported in the art but recognised by the inventors is that due to the very high circulating field present within the pump cavity the device can be operated in the pulsed regime, by the addition of a Q-switch, with very high repetition rates far in excess of what would be possible with an extra-cavity OPO without the use of a far larger pump laser. The high repetition rate capability facilitates the use of such a pulsed system with raster scanning image acquisition systems whilst maintaining reasonable framing rates. In addition, because the need to align and match a separate pump laser with the OPO is avoided as is also the need for powerful optical pump sources and their concomitant forced air/water cooling requirements, the device of the present invention is simple, compact, robust and has inherently improved mechanical stability. Indeed, by using an intracavity geometry, the detector of the invention can be provided as a handheld, battery operated device.

Preferably, the pump wave laser source is operable in a pulsed mode. This may be achieved by Q-switching the laser. This is done in order to desensitise the optical system to the loss incurred by the insertion of frequency control components, such as étalons and gratings.

Preferably, the detector is a single detector element and a raster-scanning technique is used. This is preferable to avoid the current high cost of a mid-infrared video array. Use of raster scanning techniques is possible, because the intracavity OPO can be operated at very high repetition rates without loss of efficiency. This is crucial for attaining video-like framing rates when used in conjunction with raster scanning, because one optical pulse is required for each pixel scanned. The high repetition rate enabled by an intracavity OPO enables reasonable image refresh rates of several frames per second to be achieved.

A key advantage of OPOs, both extra- and intra-cavity, is that their optical output is broadly tunable even if the parent pump laser does not necessarily exhibit tunability. The tunability of the OPO is achieved through changing various parameters associated with the nonlinear crystal upon which the OPO depends to down-convert the pump wave, such as temperature, angle or grating period in the case of periodically-poled crystals. Broad tunability is highly desirable as it allows several different absorption features to be accessed with a single device, leading to the possibility of multiple species detection from a single device simply by tuning the wavelength of the down-converted waves to match the absorption feature of interest.

BRIEF DESCRIPTION OF THE DRAWING

Various aspects of the invention will now be described by way of example only and with reference to the accompanying drawing, FIG. 1, which is a block diagram of an intra-cavity OPO imager.

DETAILED DESCRIPTION OF THE DRAWING

Figure 1:
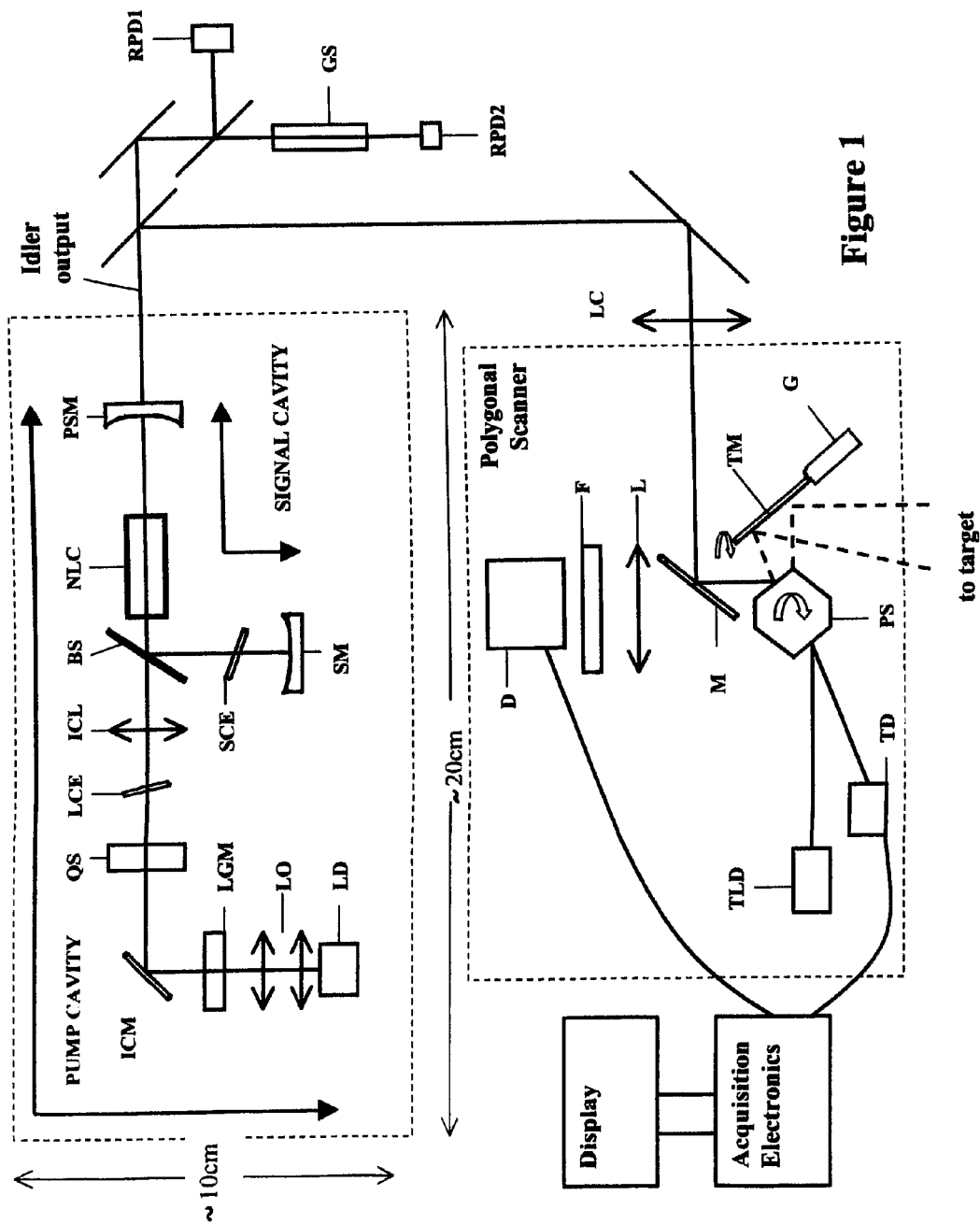

The imager of FIG. 1 has two subsystems, these being an intracavity OPO illumination source and a raster scanning image acquisition system. These are shown in separated broken boxes.
Illumination Source The intracavity OPO (ICOPO) comprises three sub-systems: a first optical cavity (pump laser cavity) containing a laser gain medium LGM that serves to provide a pump wave source for the nonlinear parametric process; an excitation source for the laser gain medium LGM, which in this case is a semiconductor diode LD; and a second optical cavity (signal cavity) that is in part common to the first said optical cavity and which contains in that common part a nonlinear crystal NLC, typically a periodically poled nonlinear crystal, which serves to generate the down converted waves. Any suitable nonlinear crystal could be used, for example PPLN or PPRTA. The pump wave source has a 1.064 μm output wavelength laser gain medium LGM, in this case a Nd:YVO$_4$ crystal, which is pumped by the laser diode LD operating at 808.5 nm. The diode LD is thermoelectrically cooled such that the wavelength of the radiation it emits is coincident with the peak absorption in the Nd:YVO$_4$ crystal. The radiation emitted by the diode LD is collimated and then focussed down into the Nd:YVO$_4$ crystal by two coupling lenses CO. Radiation emitted from the crystal is then directed onto an intra-cavity mirror ICM. On the same optical path as the intra-cavity mirror ICM are in sequence a Q-switch element QS, a laser cavity etalon LCE, an antireflection (at 1.064 μm) coated intracavity lens ICL, a beam splitter BS, the nonlinear crystal NLC, and a curved pump/signal mirror PSM. Opposite the beam splitter BS are also a signal cavity etalon SCÉ and a signal mirror SM.

The pump laser cavity is defined by the rear face of the Nd:YVO$_4$ crystal LGM, which is antireflection coated for 808.5 nm light and highly reflecting at 1.064 μm and the pump/signal mirror PSM, which is highly reflecting at 1.064 μm and broad-band highly reflecting centred at 1.550 μm. An appropriate beam waist of the pump intracavity field is formed in the nonlinear crystal NLC by the antireflection (at 1.064 μm) coated intracavity lens ICL and the curved pump/signal mirror PSM. The plane beamsplitter BS is coated on both sides to be antireflection at the pump wavelength but, on its lower face, highly reflecting at the signal wavelength. Thus, the pump/signal mirror PSM and the signal mirror SM form a signal cavity. The (mid-infrared) idler radiation is not resonated and exits the cavity through the pump/signal mirror PSM after being generated in the nonlinear crystal NLC, which is triple-band antireflection coated for the pump, signal and idler.

To facilitate tuning of the idler, the (periodically poled) nonlinear crystal NLC is held within a temperature stabilised chamber (not shown) that has a temperature can be varied if required. It should be noted that generally, the useful signal radiated by an optical parametric device is the so-called "signal" wave. In this case, however, it is the idler wave that has a more appropriate wavelength and so is allowed to exit the OPO cavity. The tuning range of the idler is limited in practice by the choice of periodic poling gratings applied to the crystal, the temperature range over which it is chosen to operate the nonlinear crystal and the reflectivity profile of the signal cavity mirrors. For detection of a single species these parameters would be optimised for operation over a small range of wavelengths, a typical example being tuning of only around 10 nm about 3.31 μm for methane detection. For multi-species detection, these parameters may be varied to provide spectral coverage over an extended range of greater than 3-4 μm Reduced linewidth in the idler wave is desirable in order to increase the sensitivity and selectivity of the instrument. The linewidth of the idler is broadened by a combination of the finite gain bandwidth in the laser gain medium and the phase-matching bandwidth of the parametric down-conversion process. Providing the étalons within both the pump LCÉ and signal cavity SCÉ facilitates some measure of line narrowing. Both étalons are very thin and need not be of high finesse and so the impact they have on their respective cavities, in terms of optical and walk-off loss, is minimised. With the inclusion of these étalons, mid-infrared linewidths of the order of 30 GHz can be obtained (reduced from a free-running linewidth of ~250 GHz). Such a line width is adequate for detectability of, for example, methane concentrations down to ~35 ppm·m when the idler wavelength is tuned into the numerous absorption lines, which become a quasi-continuum of absorption due to pressure broadening, at ~3018 cm$^{-1}$ (3.31 μm). Here, minimum detectability is defined as the concentration/path length product which leads to a 10% absorption of the optical radiation.

Using the arrangement of FIG. 1, differential imaging can be achieved. This involves acquiring two successive scans with one taken at a wavelength that coincides with the absorption feature of the species of interest, the other at a wavelength where the species exhibits little or no absorption. This allows the difference between the two acquired images (corresponding to the areas where only the species is present) to be calculated and highlighted (for example, in false colour) on the displayed image. Use of this technique mandates the capability of the idler wavelength to be rapidly switched from the on-to-off absorption condition. This is facilitated by rotating the signal cavity étalon SCÉ between scans in order to rapidly tune the signal, and hence the idler, wavelength within the phase-matched bandwidth of the parametric oscillator.

To desensitise the pump and signal cavities from the effects of optical loss brought about by the various components (particularly, the étalons), the system is Q-switched. This is facilitated by the Q-switching element QS in the 'pump-only' arm of the laser. As outlined above, the ICOPO is capable of being Q-switched at very high repetition rates due to the enhancement of the intracavity technique. The timing of the Q-switch is synchronised to the pixel acquisition of the scanning system. As noted previously, an advantage of the intracavity system is its ability to be operated at extremely high pulse repetition rates. This makes the detector appropriate for use with a raster scanning system. The intracavity system can be operated at repetition rates in excess of 250 kHz, which enables framing rates of >15 fps to be achieved with a resolution of 15,000 pixels. Typically, externally pumped pulsed OPOs are only able to achieve repetition rates on the order of ~15 kHz which would lead to a frame acquisition time of 1 second for the same pixel resolution.

In order to ensure the idler wavelength is optimised for maximum absorption of the spectroscopic feature of interest a small proportion of the idler output can be picked off and passed through a reference sample, for example a gas cell GS. The absorption of the cell is measured by two photodetectors RPD1 and RPD2. If the expected absorption is not realised then an on board servo-loop will tune the idler wavelength via a combination of the nonlinear crystal temperature and signal cavity étalon tilt angle. The photodetector RPD1 can also be used to measure the shot-to-shot variation in idler intensity and can then normalise the backscattered signal, which results in reduced noise and higher sensitivity in the acquired image.

The Scanner

Radiation from the optical parametric oscillator is directed from the optical parametric device into the scanner using various mirrors. Along an optical axis of the scanner is a small plane mirror m placed on-axis in front of a collimating lens LC, which is fabricated from a material which exhibits high transmission over the 3-4 μm range, for example calcium fluoride. From the mirror m, radiation is directed via a rotating polygon scanner PS and tilting mirror TM to the scene under surveillance. The back-scattered radiation returning from the scene is collected via the same tilting mirror and polygon scanner and is then focused by a collection lens L onto the single element detector D located in its image plane. The area of the collection lens L is sufficient such that the effective limiting collection aperture for the returned signal occurs at the polygon mirror facet. This arrangement ensures that the detector always views that area of the scene currently being illuminated by the scanned radiation from the optical parametric oscillator, i.e. the viewing direction is scanned in spatial synchronism with the illuminating beam.

The calcium fluoride lens LC placed before the mirror m allows independent adjustment of the focusing of the illuminating radiation on the chosen target. In particular it allows the projection of a beam waist onto the target area so as to optimise the spatial resolution of the scanner in relation to the response time of the detector and the lateral extent of the area being scanned. Since the detector employed exhibits sensitivity over a broad range of wavelengths, a band pass filter F is placed in close proximity to the detector active area in order to reject stray infrared radiation from hot objects, lights and pump and signal fields that are leaked through OPO mirror PSM.

Connected to the detector D are the acquisition electronics, which in turn are connected to a display and a trigger detector TD. Associated with the trigger detector is a low power laser diode TLD. The low power laser diode TLD is positioned to direct light onto the rotating polygon. Radiation reflected from the polygon falls on the detector TD at a pre-determined trigger position. Detection of light by the detector TD is used to trigger the image acquisition electronics at the correct point of the polygon rotation when scanning a horizontal line. When the trigger signal is received, the acquisition electronics capture data from the detector D, process that data and provide a real-time image of the target scene. Software for doing the required image processing is known and so will not be described in detail.

The polygon scanner PS provides line scanning of the illuminating beam in a horizontal direction. The tilting mirror TM provides scanning in the orthogonal (vertical) direction, and is set up so as to provide beam deflection over an angle of similar to that of the polygon scanner. The rotational speed of the polygonal scanner is such that the maximum bandwidth of the detector D and the subsequent acquisition electronics are not exceeded. In use, a trigger signal from the acquisition electronics is fed to the Q-Switch in order to emit a mid-infrared idler pulse for every pixel acquired. Therefore, the maximum rate at which the Q-switch could be triggered determines the upper ceiling of the framing rate that can be obtained from the system.

Variations of the arrangement of FIG. 1 are possible. For example, for greater narrowing of the signal (and hence the idler), the signal mirror SM and étalon SCÉ may be exchanged for a collimating lens and optical diffraction grating. Such an arrangement would give more frequency selectivity to the desired signal wavelength than the low finesse étalon arrangement outlined previously. Careful adjustment of the grating angle with respect to the optical axis of the signal cavity facilitates fine tuning of the signal, and hence the idler, wavelength. An idler linewidth of ~30 GHz can be attained with this arrangement. For even greater linewidth reduction and hence greater sensitivity, an étalon could be included in the signal cavity of this arrangement. This would give very narrow linewidths, down to 3 GHz, i.e. typically less than or comparable to the pressure-broadened linewidth of a single spectral absorption feature. The much-narrowed signal field provided by the diffraction grating allows the use of a lower free spectral range, and hence higher finesse, étalon without the need of increasing the reflectivity of the étalon coatings. Because the idler linewidth can be reduced to 3 GHz, this allows the selection of a single absorption line in the species of interest. For maximum sensitivity the spectral line that exhibits the greatest absorption would be chosen. For example, in the case of methane, this absorption line is located at 3057.7 cm$^{-1}$ (3.27 μm). The selection of this line increases sensitivity to the point that gas concentrations as low as ~10 ppm·m can be imaged.

By removing the Q-switching (QS) element from the pump only arm of the device, continuous-wave operation of the intracavity OPO would be realised. This removes the upper framing rate limit imposed upon the polygonal scanning system as the requirement for ever higher repetition rates is removed. The continuous-wave nature of the device would also lead to very narrow line widths <100 MHz provided sufficient narrowing of the circulating pump field is achieved and a frequency control element is included in the signal cavity to stabilise the absolute frequency of the single-mode signal wave.

The device described is ideally suited for vehicular mounting for the rapid surveying of large areas. At a pulse repetition rate of ~250 kHz, a direct-absorption measurement across the width of the vehicle could be achieved every ~0.1 mm of road distance traveled at a speed of 60 mph. This would effectively lead to continuous sampling over the surveyed area. By incorporating the scanning system (which would possibly omit the galvanometer G and tilting mirror TM as y-axis separation is now afforded by the forward movement of the vehicle), a continuous spatial survey of the road surface could be achieved. The spatial resolution of such a survey would be ~10 mm assuming a resolution of 100 pixels.

Increasing the output power of the illuminating radiation can further reduce the image acquisition time or increase the range of operation and hence would enable its use for very rapid surveying of extremely large installations such as continental pipelines by its airborne use in a helicopter/aeroplane. Equally, the imager in which the invention is embodied could be used in seaborne vehicles.

The detector of the present invention is efficient and capable of producing significant optical powers. The high repetition rate capability facilitates the use of a raster scanning image acquisition system, whilst maintaining reasonable framing rates. Because the need to align and match a separate pump laser with the OPO is largely mitigated as is the need for powerful optical pump sources and their concomitant forced air/water cooling requirements, the device of the present invention is simple, compact, robust and has good inherent mechanical stability. Also, because the intracavity optical parametric device can be made small (for example 10 cm by 20 cm as shown in FIG. 1), the detector of the invention can be provided as a handheld, battery operated device.

A skilled person will appreciate that variations of the disclosed arrangements are possible without departing from the invention. For example although FIG. 1 shows an intra-cavity mirror ICM and various mirrors for directing radiation from the OPO into the scanner, these are optional and are included to reduce the overall footprint of the device. Also, the detector may be operable to identify species, as well as detect species. To this end, the detector may, for example, include or have access to stored information, such as calibration information, relating to one or more specific species and may be operable to compare sensing data captured by the detector with the stored information, thereby to identify the species detected. Also, whilst in the embodiment described with reference to FIG. 1, the idler wave is used as the sensing radiation, it will be appreciated that in some circumstances, the signal wave my be used instead. The selection of which wave to use would depend on the species that is to be sensed. In addition, although the specific examples described relate to the detection of methane, the detector of the invention can be used to detect other gases. In addition, the detector can be used to detect liquids and/or solids and/or plasmas. Accordingly the above description of the specific embodiment is made by way of example only and not for the purposes of limitation. It will be clear to the skilled person that minor modifications may be made without significant changes to the operation described.

The invention claimed is:

1. A back scatter absorption detector/imager having an optical parametric device for generating sensing radiation, the optical parametric device having a laser gain medium for generating a pump wave in a pump wave cavity and a nonlinear medium and a pump wave laser source, the nonlinear medium generating a signal and an idler wave in response to being stimulated with the pump wave, thereby to generate sensing radiation, and a detector external to the pump wave cavity that detects sensing radiation back-scattered from a target area, wherein the laser gain medium and the nonlinear medium are located in the pump wave cavity, and a Q-switch element is included in the pump wave cavity to cause the optical parametric device to operate in a pulsed mode.

2. A detector/imager as claimed in claim 1 wherein the optical parametric device is operable to emit radiation with a pulse repetition frequency of more than 100 kHz.

3. A detector/imager as claimed in claim 1 wherein an etalon is provided in a pump wave in only part of an optical path between a laser gain medium and the nonlinear medium.

4. A detector/imager as claimed in claim 1 wherein a beam splitter is provided on an optical path between a laser gain medium and the nonlinear medium to direct the signal wave into a signal wave only optical path.

5. A detector/imager as claimed in claim 4 wherein an etalon is provided in the signal only optical path.

6. A detector/imager as claimed in claim 5 wherein a signal minor is provided behind the etalon for directing signal radiation back towards the beam splitter.

7. A detector/imager as claimed in claim 4 wherein a collimating lens and optical diffraction grating are provided in the signal only optical path, the lens being positioned between the beam splitter and the diffraction grating.

8. A detector/imager as claimed in claim 1 including a scanner for directing the sensing radiation from the optical parametric device to scan the target area with the sensing radiation and to direct sensing radiation reflected from that target area towards the detector.

9. A detector/imager as claimed in claim 8 wherein the scanner is raster scanner.

10. A detector/imager as claimed in claim 8 wherein the scanner includes a rotatable, polygon mirror for directing sensing radiation towards the detector.

11. A detector/imager as claimed in claim 1 including means for displaying an output from the detector in the form of an image of the target area.

12. A detector/imager as claimed in claim 1 that is handheld/portable.

13. A detector/imager as claimed in claim 1 that is battery powered.

14. A detector/imager as claimed in claim 1 operable to sense a solid and/or a liquid and/or a gas and/or a plasma.

15. A detector/imager as claimed in claim 1 that includes or has access to stored information relating to one or more specific species and is operable to compare sensing data captured by the detector with the stored information, thereby to identify a species present in the target area.

16. A detector/imager as claimed in claim 1 including means for tuning the sensing radiation.

17. A vehicle comprising the detector imager of claim 1 mounted on the vehicle, wherein the vehicle is one of airborne, seaborne and landborne.

* * * * *